United States Patent [19]

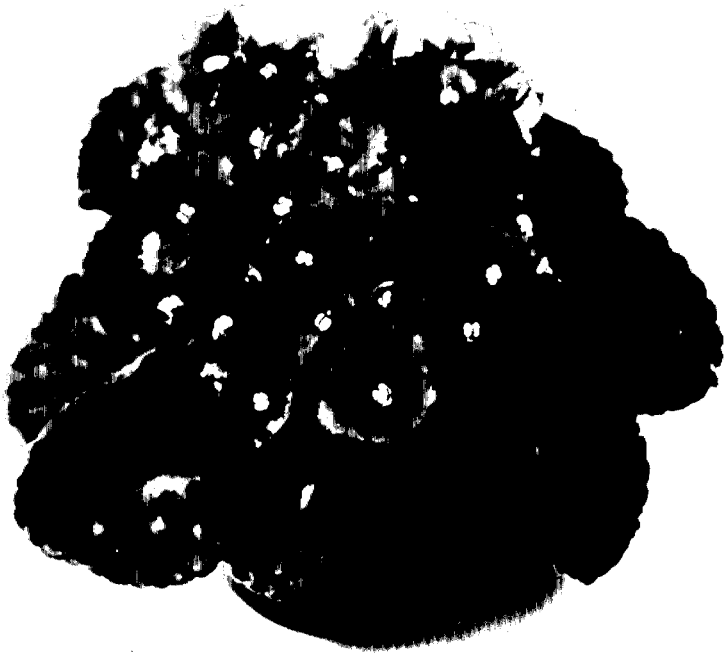

Holtkamp

[11] Patent Number: Plant 5,700

[45] Date of Patent: Mar. 25, 1986

[54] AFRICAN VIOLET PLANT NAMED IMPROVED ORLANDO

[75] Inventor: Reinhold Holtkamp, Isselburg, Fed. Rep. of Germany

[73] Assignee: Gessellschaftsvertrag uber die Ergindergemeinschaft "OPTIMARA", Fed. Rep. of Germany

[21] Appl. No.: 568,449

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet plant named Improved Orlando particularly characterized by its compact growth habit, girl-type leaves, short, sturdy and upright flower stems each carrying 7 and more violet shaped and frilled flowers, intensive violet blue flower color, compact flower bouquet, long lasting and non-dropping flowers, and by its ability to produce a saleable plant in 9–10 weeks after potting.

1 Drawing Figure

The present invention comprises a new and distinct cultivar of African violet plant, botanically known as *Saintpaulia ionantha,* and named Improved Orlando.

The new cultivar was referred to during the breeding and selection process by the designation G 13/III, and is a product of a planned breeding program.

The new cultivar was originated from a cross made in a controlled breeding program in Isselburg, West Germany. The female, or seed parent was a cultivar designated d 150/2 red girl frilled. The male, or pollen parent was a cultivar designated 26 blue single.

The new cultivar Improved Orlando was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Improved Orlando has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Improved Orlando, which in combination distinguish this African violet as a new and distinct cultivar:

1. Compact growth habit.
2. Attractive girl type leaves having bright green centers.
3. Relatively short, sturdy and upright flower stems each of which carries seven or more flowers.
4. Ruffled flower form, with frilled edges.
5. The flowers are intense blue in color.

The new cultivar is most similar to the cultivar Orlando, a commercially known but unpatented cultivar. The new cultivar is principally distinguished from Orlando by its shorter and stronger stems, darker flower color and more ruffled flower form, and by its darker leaves.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately 9 A.M. in late November in Nashville, Tenn. When grown under relatively cooler conditions, the plant will be more intensive in flower color, and under relatively higher finishing temperatures, a slight fading in flower color will appear.

Botanical classification: *Saintpaulia ionantha,* Ramat. cv Improved Orlando.

Parentage:

*Male parent.*—25 Blue single.

*Female parent.*—d 150/2 Red girl frilled.

Propagation: The new cultivar holds its distinguishing characteristics through successive propagations by leaf cuttings and by division of shoots.

Plant: From 7 cm. to 9 cm. tall when grown in pots, and approximately 15–18 cm. in diameter when fully grown.

*Leaves.*—General Form: Round girl-type leaves. Diameter: 55–60 mm. Texture: Velvety. Aspect: Slightly shiny and hairy. Veins: From underside, visibly light green, shiny and hairy. Color (upperside): Yellow green 147A, with bright green center. Color (underside): Yellow green 148D. Petiole: Brownish, green, hairy.

*Flowers.*—Buds: Ball shape. Sepals: 5 Color: Brownish green tips. Calyx: Flat funnel. Aspect: Greenish brown, spear-shape. Peduncle: Short wire-like and upright; hairy.

*Individual flowers.*—Size: 35–40 mm. Color: Upperside: Violet blue 90A. Underside: Violet blue 90C. Borne: On relatively short, upright flower stems which form compact bouquet. Shape: Violet-like, frilled, ruffled. Corolla: Compact flower head; 7–9 flower stems. Flowering time: 10 weeks after potting a saleable full flowering plant is formed.

*Reproductive organs.*—Anthers: 2 composed of 4 cells. Filaments: Light green, hairy. Styles: Deep purple.

*Roots.*—White when young and active; brownish when older.

*Disease resistance.*—Good as experienced to date.

General observations: Improved Orlando is a compact growing girl type variety with velvet and slightly shiny leaves. Out of the center 7–9 or more short, sturdy and upright flower stems are formed each of which carry 7 and more deep purple blue frilled violet shape flowers thereby forming a compact flower bouquet. The flowers are long lasting and do not drop, and a saleable plant is produced in 9–10 weeks after potting.

I claim:

1. A new and distinct cultivar of African violet plant named Improved Orlando, as described and illustrated, and particularly characterized by its compact growth habit, girl-type leaves, short, sturdy and upright flower stems each carrying 7 and more violet shaped and frilled flowers, intensive violet blue flower color, compact flower bouquet, long lasting and non-dropping flowers, and by its ability to produce a saleable plant in 9–10 weeks after potting.

* * * * *